(12) United States Patent
Kagermeier et al.

(10) Patent No.: US 10,820,879 B2
(45) Date of Patent: Nov. 3, 2020

(54) METHOD FOR OPERATING A COLLIMATOR OF AN X-RAY DEVICE AND X-RAY DEVICE

(71) Applicant: Siemens Healthcare GmbH, Erlangen (DE)

(72) Inventors: Robert Kagermeier, Nuremberg (DE); Gerben Ten Cate, Forchheim (DE); Asa MacWilliams, Fuerstenfeldbruck (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 213 days.

(21) Appl. No.: 16/190,270

(22) Filed: Nov. 14, 2018

(65) Prior Publication Data
US 2019/0150874 A1 May 23, 2019

(30) Foreign Application Priority Data

Nov. 17, 2017 (DE) .......................... 10 2017 220 529

(51) Int. Cl.
*A61B 6/00* (2006.01)
*A61B 6/06* (2006.01)
*A61B 6/04* (2006.01)

(52) U.S. Cl.
CPC ................ *A61B 6/548* (2013.01); *A61B 6/06* (2013.01); *A61B 6/4464* (2013.01); *A61B 6/462* (2013.01);
(Continued)

(58) Field of Classification Search
CPC ......... A61B 6/548; A61B 6/467; A61B 6/566; A61B 6/547; A61B 6/4464; A61B 6/06;
(Continued)

(56) References Cited

U.S. PATENT DOCUMENTS

2016/0242716 A1* 8/2016 Dinse ..................... A61B 6/467
2019/0150876 A1* 5/2019 Kagermeier ......... A61B 6/4464

FOREIGN PATENT DOCUMENTS

DE 102013219194 A1 3/2015
DE 102014205671 A1 10/2015

OTHER PUBLICATIONS

Philips: Indoor Positioning White paper: Unlocking the value of retail apps with lighting.

* cited by examiner

*Primary Examiner* — Michael C Bryant
(74) *Attorney, Agent, or Firm* — Harness, Dickey & Pierce, P.L.C.

(57) ABSTRACT

A method is for a medical imaging X-ray device including an X-ray generator, to which the collimator is assigned, an X-ray detector, a patient table for positioning a patient to be X-rayed, and a wireless, hand-held operator device including a touchscreen. In an embodiment, the method includes generating a display, visualizing a current setting of the collimator, on the touchscreen; adjusting the collimator according to operating data describing a manipulation of display elements of the display; determining position information, describing at least one of a position and orientation of the operator, from sensor data of at least one sensor; selecting a perspective, using the position information determined, corresponding at least approximately to a viewing angle of an operator with respect to the patient table; and generating the display for three-dimensionally visualizing, showing an X-ray beam with the collimator settings adjusted, at the perspective selected.

18 Claims, 4 Drawing Sheets

(52) U.S. Cl.
CPC .............. *A61B 6/463* (2013.01); *A61B 6/467* (2013.01); *A61B 6/469* (2013.01); *A61B 6/547* (2013.01); *A61B 6/566* (2013.01); *A61B 6/0407* (2013.01)

(58) Field of Classification Search
CPC ......... A61B 6/462; A61B 6/463; A61B 6/469; A61B 6/0407
See application file for complete search history.

10,820,879 B2

METHOD FOR OPERATING A COLLIMATOR OF AN X-RAY DEVICE AND X-RAY DEVICE

PRIORITY STATEMENT

The present application hereby claims priority under 35 U.S.C. § 119 to German patent application number DE 102017220529.6 filed Nov. 17, 2017, the entire contents of which are hereby incorporated herein by reference.

FIELD

Embodiments of the invention generally relate to a method for operating a collimator of an X-ray medical imaging device which has an X-ray generator to which the collimator is assigned, an X-ray detector, a patient table for positioning a patient to be X-rayed, and a wireless, hand-held operator device having a touchscreen. In at least one embodiment, a display showing the current collimator setting is generated on the touchscreen and the collimator is adjusted according to operating data describing a manipulation of display elements of the display. At least one embodiment of the invention also relates to an X-ray device.

BACKGROUND

For medical X-ray imaging it is now commonplace to use collimators for limiting the beam of the X-ray generator according to the desired image acquisition. This serves to prevent both the patient from being exposed to unnecessary radiation and also blooming of the X-ray image if there is a lack of X-ray attenuation due to air gaps.

A corresponding collimator, usually mounted downstream of the X-ray generator and upstream of the examination subject, can comprise different collimator elements which can be adjusted, e.g. by corresponding actuators, in order to delimit the required X-ray field. For example, a beam can be coned down using lead leaves as collimator elements. To adjust the collimator or rather the collimator elements it is specifically known, for example, to use manual rotary knobs directly on the collimator housing (near patient) and/or operator control buttons on a local/remote control device. For operator control directly on the collimator, in particular using rotary knobs, the operator observes the degree of beam limiting, e.g. by way of light projection from the collimator via which the narrowed X-ray beam is visualized. The operator here uses his/her hands away from the patient on the collimator which is usually located above the patient together with the X-ray generator. This results in less than optimal hand-eye coordination.

If a mobile operator device and/or operator control buttons are used, this also constitutes a somewhat less intuitive and pleasant mode of operation. This applies in particular when the operator actuates the different control elements from different positions around the patient table, as these work on the basis of a preferred position, and an expected opening of the horizontal or vertical aperture is only produced correctly from this preferred position. The operator must here mentally perform an orientation correction, which has to be rated inconvenient from a usability point of view.

DE 10 2014 205 671 A1 relates to a generic device for collimator control. A display unit for displaying a representation of the collimator is used, wherein an input unit is additionally provided which can be implemented as a touchscreen. The representation of the collimator can include of an image of the collimator which can be simplified or rather schematized. On the touchscreen it is proposed to allow displacement by dragging the representation on the touchscreen, enlargement or reduction via a pinching gesture and corresponding combinations. In particular, a section of the patient can be displayed with an area which corresponds to the beam set by the collimator.

SUMMARY

At least one embodiment of the invention specifies a more intuitive and simpler way of adjusting a collimator for an X-ray imaging device.

At least one embodiment of the invention is directed to a method, wherein position information describing the position and/or orientation of the operator is determined from sensor data of at least one sensor and used to select a perspective corresponding at least approximately to the operator's angle of view of the patient table for the three-dimensionally visualizing display showing the beam with the current collimator settings.

It is also proposed according to at least one embodiment of the invention, to use a mobile, wireless, hand-held operator device which is preferably implemented as a smart device, i.e. in particular as a smartphone and/or a tablet.

At least one embodiment of the invention is directed to a method for operating a collimator of a medical imaging X-ray device including an X-ray generator to which the collimator is assigned, an X-ray detector, a patient table for positioning a patient to be X-rayed, and a wireless, hand-held operator device having a touchscreen, wherein a display visualizing the current setting of the collimator is generated on the touchscreen and the collimator is adjusted according to operating data describing a manipulation of display elements of the display. In at least one embodiment of the method, position information describing the position and/or orientation of the operator is determined from sensor data of at least one sensor and used to select a perspective corresponding at least approximately to the operator's viewing angle with respect to the patient table for the three-dimensionally visualizing display showing the X-ray beam with the current collimator settings.

In addition to the method, at least one embodiment of the present invention also relates to an X-ray device having an X-ray generator to which a collimator is assigned, an X-ray detector, a patient table for positioning the patient to be X-rayed, a wireless hand-held operator device having a touchscreen, and a control device designed to carry out the method according to at least one embodiment of the invention. All statements in respect of embodiments of the inventive method can be applied analogously to embodiments of the inventive X-ray device with which the already mentioned advantages can therefore likewise be achieved.

BRIEF DESCRIPTION OF THE DRAWINGS

Further advantages and details of the present invention will emerge from the example embodiments described below and with reference to the accompanying drawings in which.

DETAILED DESCRIPTION OF THE EXAMPLE EMBODIMENTS

Figure 1:
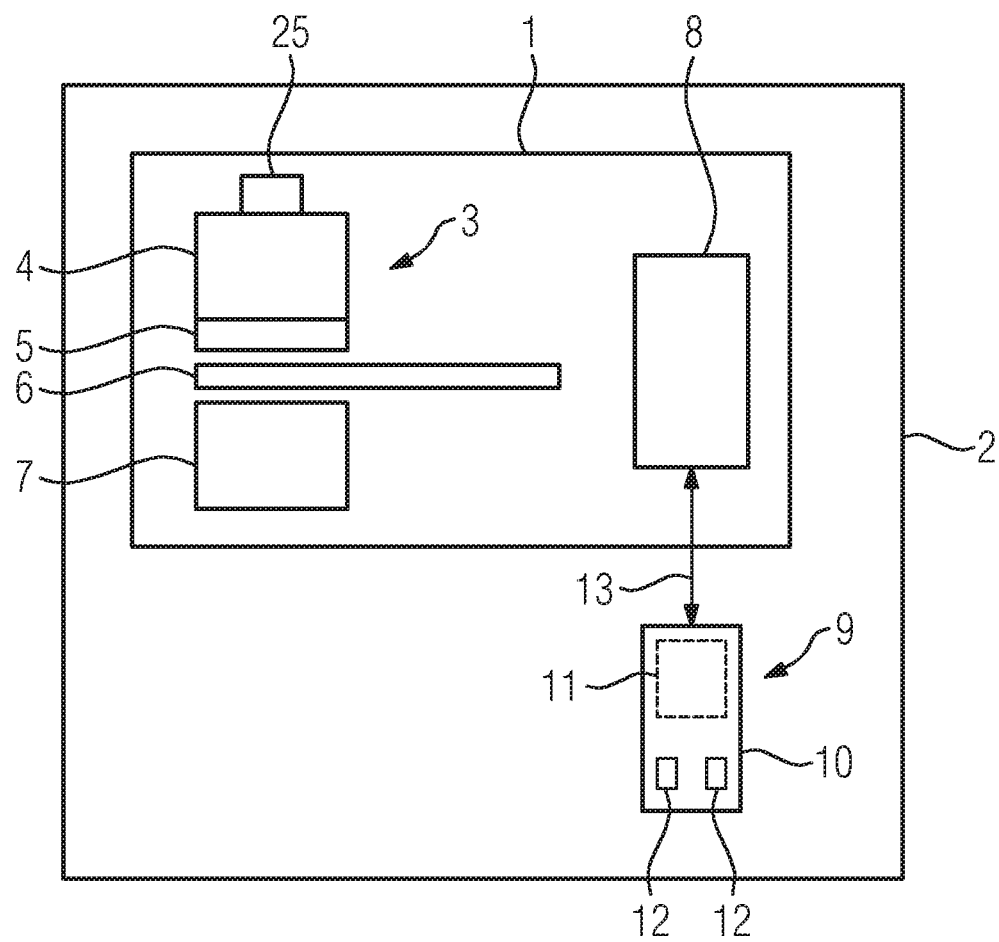
FIG. 1 shows a schematic diagram of an X-ray device according to an embodiment of the invention in a room.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention is directed to a method, wherein position information describing the position and/or orientation of the operator is determined from sensor data of at least one sensor and used to select a perspective corresponding at least approximately to the operator's angle of view of the patient table for the three-dimensionally visualizing display showing the beam with the current collimator settings.

The operator device can be taken to different positions in the room in which the X-ray device is disposed, thereby producing different suitable perspectives for intuitive control of the collimator settings. It is now inventively proposed to track at least the rough position of the operator carrying the operator device in the room and to take this into account for generating the display on the touchscreen in order to select a corresponding suitable perspective. By way of the position information, a 3D representation of the collimator setting, in particular in the form of an X-ray beam, can be visualized on the mobile operator device, the representation corresponding to the real operator view with respect to the patient. While the operator therefore has both the patient and the collimator settings in his/her field of vision, intuitive control of the collimator by the operator can be achieved. The intuitiveness and ease of operation is enhanced still further by the use of a touchscreen which allows direct manipulation of the display elements relating to the X-ray beam in order to vary the collimator settings accordingly.

While it is basically conceivable within the scope of at least one embodiment of the present invention to determine the position information by detecting and tracking the operator him/herself in sensor data of an operator-detecting operator sensor, in particular to determine the position information from sensor data of an operator-tracking camera, at least one embodiment of the present invention provides that position data comprising a position and/or an orientation of the operator device is determined via the at least one sensor, wherein the position information is derived from the position data using at least one assumption in respect of the operator, in particular the operator's height and/or viewing direction. This embodiment is particularly advantageous, since the position data relating to the operator device, in particular a smart device, can also be used for other operating functions of the operator device, e.g. to control the movement of movable components of the X-ray device and the like. As the operator is holding the operator device in his/her hand, the operator's position, in particular the position of the operator's eyes, can therefore be easily inferred from the position and possibly orientation of the operator device, for which, for example, corresponding assumptions can be made.

It should be pointed out that, based on at least one embodiment of the inventive method which will be examined in greater detail below, it may also be sufficient to assume that the position of the operator device is also the position of the operator, as it has already been shown that an essential factor in respect of intuitive operator control is the orientation relative to the patient table, and even for evaluating a rough position a clear improvement in usability is already made possible by the selection of a suitable perspective.

The operating data can preferably be determined from the sensor data of at least one operator device sensor incorporated in the operator device. Especially if, as is preferable, a smart device is used as the operator device, such smart devices already have appropriate operator device sensors which, in the context of the present invention, expediently provide suitable sensor data for determining the position data and therefore the position information.

Thus, in an advantageous embodiment of the present invention, it can be provided that at least one operator device sensor is a camera, in the image data of which optical markers disposed in the room in which the X-ray device is disposed are detected and used to determine the position data. In particular, it can be provided that the operator device has two cameras, in particular a front camera and a rear camera, which during normal use of the operator device are also oriented such that a corresponding amount of the room and therefore of the optical markers proposed here can be covered. The markers are captured continuously by the at least one camera usually present anyway in the operator device and analyzed, wherein for this purpose the operator holds the operator device in its natural handling mode, i.e. does not need to adopt a searching posture for the camera of the operator device.

The position of the respective optical markers in the room can be precisely determined during a configuration phase and made known in the control device carrying out the evaluation, i.e. in particular the control device of the medical technology device and/or the control device of the operator device. Specifically it is conceivable, for example, to use passive optical markers, e.g. printed stick-on labels, and attach them to the ceiling, walls and/or floor of the room in which the X-ray device is located, wherein in particular it is also conceivable for optical markers generally to be attached to the X-ray device itself.

However, an example embodiment of the present invention provides that active markers, in particular comprising visible-light and/or infrared LEDs are used as at least some of the markers. It is particularly expedient here if, for position determination, the active markers are caused to operate by the operator device via a short-range radio link, in particular a Bluetooth connection. Optimized detection of the optical markers can therefore be achieved by active and synchronized markers (optical beacons). Synchronization can take place via the short-range radio interface, e.g. Bluetooth Low Energy (BLE), likewise normally already present in smart devices. By active control of brightly illuminated active markers, in particular brightly illuminated infrared LEDs of the markers, significantly better detection of the optical markers can be implemented. As explained, these optical markers expediently are or become synchronized with the operator device sensors.

In this context, an expedient development of at least one embodiment of the invention provides that the position data is determined at least partially according to a signal delay method and/or on the basis of a field strength of the radio signals emitted by the markers in the case of a bidirectional short-range radio link. If the active markers implemented e.g. as optical beacons are designed for direct communication with the operator device via a separate short-range radio interface, they also create, in addition to the optical marker characteristics, radio markers (in particular radio beacons) which can already contribute to at least coarse position determination of the operator device in the room, e.g. by measurement of the delay of radio signals and/or the strength thereof. The corresponding field strengths (receive strengths) in the room can be determined in a configuration phase, as has been proposed, for example, in a BLE beacon concept of the Fujitsu company.

Even in an embodiment in which no short-range radio link to active optical markers is set up, a similar functionality with rough position determination can be provided. In this case the actively light-transmitting optical markers are operated as light beacons. For this purpose it can be provided that the actively light-transmitting optical markers emit a marker-specific identification signal which is modulated onto the light and is evaluated by the receiving operator device. On the basis of the identification signals detected in the sensor data of the camera, rough position determination can take place which may even be adequate. Such a technology has already been proposed in the prior art for locating purposes, e.g. in supermarkets, by the Philips Lighting company (White Paper "Indoor positioning").

In particular in addition to the at least one camera, at least one accelerometer and/or at least one angular rate sensor and/or at least one magnetometer, in particular as a compass, can preferably be used as an operator device sensor, wherein in particular the position data is determined at least partially by dead reckoning. It is particularly expedient in the context of the present invention if the tracking of the orientation and position of the smart device is supported by dead reckoning (inertial navigation). For example, if optical marker detection temporarily fails due to unfavorable viewing angles or is obstructed, the position data can still continue to be determined.

In a particularly advantageous embodiment of the present invention, it can be provided that the display is generated assuming a viewing direction aligned to a reference point on the X-ray device. As has already been indicated, it has been shown in developing the present invention that taking into account the position of the operator relative to the X-ray device, in particular in respect of the patient table, is essential for selecting a suitable perspective, so that the resulting viewing direction from the position described by the position information to a reference point of the X-ray device can accordingly also at least partially define a perspective from which the display on the touchscreen is generated. In this way, for example, irrespective of which side of the X-ray device/patient table the operator is located, an appropriately matched, perspective display is produced which can be intuitively brought into accordance with the real, perceived situation on the patient table, thereby enabling the collimator to be adjusted in a simple, quick and reliable manner.

Specifically, it can be provided that a central point of the patient table and/or a point of intersection of the central ray with the patient table is selected as a reference point. It is assumed here that, while controlling the collimator, the operator will direct his attention to the region of interest of the patient positioned on the patient table, wherein here the simply determinable center of the patient table can be used, but also, depending on the adjustability of the patient table or rather of the imaging arrangement, the point where the central ray is incident on the patient table can be selected dynamically. Self-evidently other reference points of the X-ray device, the position of which in the room relative to the details of the position information can be determined, can also be used.

In a specific, preferred embodiment of the present invention it can be provided that a ring of possible observation points around the reference point is defined, the observation points defining perspectives that can be selected together with the viewing direction toward the reference point, wherein the perspective described by the nearest observation point to the position described in the position information is selected. The corresponding observation point having the viewing direction in the direction of the reference point therefore defines the perspective from which the display is generated. The ring need not necessarily be circular, but can also, for example, describe an ellipse taking the elongated shape of the patient table into account. It has been found that such a limitation of the possible observation points as lying on a ring which in particular has at least one fixed and/or dynamically determinable radius and/or one fixed and/or dynamically determinable height above the floor is sufficient, as smaller deviations from the actual eye position of the operator are barely noticeable, yet the intuitiveness of the display is maintained. The height and/or the at least one radius of the ring can be selected, for example, such that a display that is clearly identifiable, intuitively readable and showing all the relevant details is produced, making it possible in particular to permanently select these values and therefore already have the basis of the displays available or else at least be able to compute them quickly, so that computing time and/or computing complexity can be expediently reduced and useful displays can be provided for the operator.

However, it is also conceivable to select the position of the ring according to the actual operator. Thus it can be provided that the height of the ring is selected according to operator height information which is predefined and/or derivable from the sensor data and/or can be specified by the operator. For example, the height of the operator's eyes above floor level can be derived or estimated from the sensor data, in particular when it also shows the operator him/herself, in order to match the operator's perspective as precisely as possible. An input or retrieval from user profiles or similar are also possible. Accordingly, the at least one radius can also be predefined empirically or in an optimally fixed manner, but it is also quite conceivable to work with the position information in respect of the at least one radius of the ring and to adjust the ring in a suitably dynamic manner according to the position information to the distance from the reference point as described by the position information.

In respect of the actual control of the collimator settings by the operator, in a specific embodiment it can be provided that when the operator manipulates the corner points of the beam shown in the display the collimator settings are adjusted to a corresponding beam geometry and/or when the operator drags the beam in the display a corresponding displacement of the collimator components is carried out. In principle the operator control options already described in DE 10 2014 205 671 A1, the entire contents of which are hereby incorporated herein by reference, can also be implemented within the scope of the embodiments of the present invention.

For example, intuitive collimator control by the operator can be achieved by touching a sensitive corner point of the beam symbolized e.g. as a collimator setting rectangle, dragging the corner point on the touch surface and transmitting this control information in real time to the control device of the X-ray device. By touching the displayed beam centrally and dragging the entire beam on the touch surface, control information can be derived which, for example, allows the combined X-ray generator and collimator unit provided with corresponding actuators to be moved so that intuitive fine correction of the region of interest can be performed. In particular, the X-ray generator and collimator are therefore implemented as one unit which can be adjusted by corresponding actuators, which can likewise be achieved by manipulating the display on the touchscreen of the operator device. Self-evidently, over and above these examples, the touchscreen provides further specific operator control possibilities from which corresponding control information can be derived.

A development of at least one embodiment of the invention provides that, for generating another additionally shown and/or alternatively selectable display containing a beam, image data of an overhead view camera disposed on the X-ray generator and/or collimator and oriented in the direction of the central ray of the X-ray generator is acquired and the additional display is generated from the point of view of the X-ray generator onto the region of interest. The X-ray generator and the collimator are again preferably implemented as one unit on which the overhead view camera displaying the view onto the region of interest from the angle of view of the X-ray generator is accordingly disposed. In this way the operator can be supplied with even more visual information, thereby altogether aiding intuitive collimator control.

In addition to the method, at least one embodiment of the present invention also relates to an X-ray device having an X-ray generator to which a collimator is assigned, an X-ray detector, a patient table for positioning the patient to be X-rayed, a wireless hand-held operator device having a touchscreen, and a control device designed to carry out the method according to at least one embodiment of the invention. All statements in respect of embodiments of the inventive method can be applied analogously to embodiments of the inventive X-ray device with which the already mentioned advantages can therefore likewise be achieved.

FIG. 1 shows a greatly simplified schematic diagram of a medical imaging X-ray device 1 which is disposed in a room 2. The X-ray device 1 comprises, as components, at least one integral unit 3 incorporating an X-ray generator 4 and a thereto assigned collimator 5, a patient table 6 and an X-ray detector 7. The operation of the X-ray device 1 is controlled by a control device 8.

At least some of the components of the X-ray device 1 are movable, i.e. generally adjustable. Corresponding actuators for implementing the respective adjustability supply signals to the control device 8 which therefore knows the current settings of the respective components. The control device 8 can simultaneously generate control signals to the corresponding actuators to make adjustments.

The collimator 5 has adjustable elements for focusing an X-ray beam defined by the settings of the collimator 5 on a region of interest. Individually controllable lead leaves, for example, can be provided as collimator elements. The collimator 5 is therefore disposed between the patient to be examined and the X-ray generator 4 on the beam path between the X-ray generator 4 and the X-ray detector 7. It is used to achieve sufficiently good image quality, e.g. by preventing blooming, and to limit the radiation dose to that necessary for the patient.

For operator control of the collimator 5, but also of other components of the X-ray device 1, the X-ray device 1 also has a wireless, hand-held, mobile operator device 9 which is implemented as a smart device 10, in this case a smartphone. The operator device 9 has touchscreen 11 as a display and input device(s); in addition, a plurality of operator device sensors 12 are provided which can comprise, for example, a front camera and a rear camera, accelerometers, angular rate sensors and at least one magnetometer. A communication link 13 to the control device 8 can be established via an appropriate radio interface (not shown in greater detail here) such as a Bluetooth interface and/or a WLAN interface. Self-evidently, parts of the control device 8 can also be implemented by a control unit of the operator device 9.

The control device 8 is now in particular also designed to determine position data which describes the position and possibly also the orientation of the operator device 9 in the room 2. For this purpose the operator device sensors 12 are used, in particular the camera in conjunction with the optical markers 14 distributed around the room 2, as will now be explained in greater detail with reference to FIG. 2.

Figure 2:
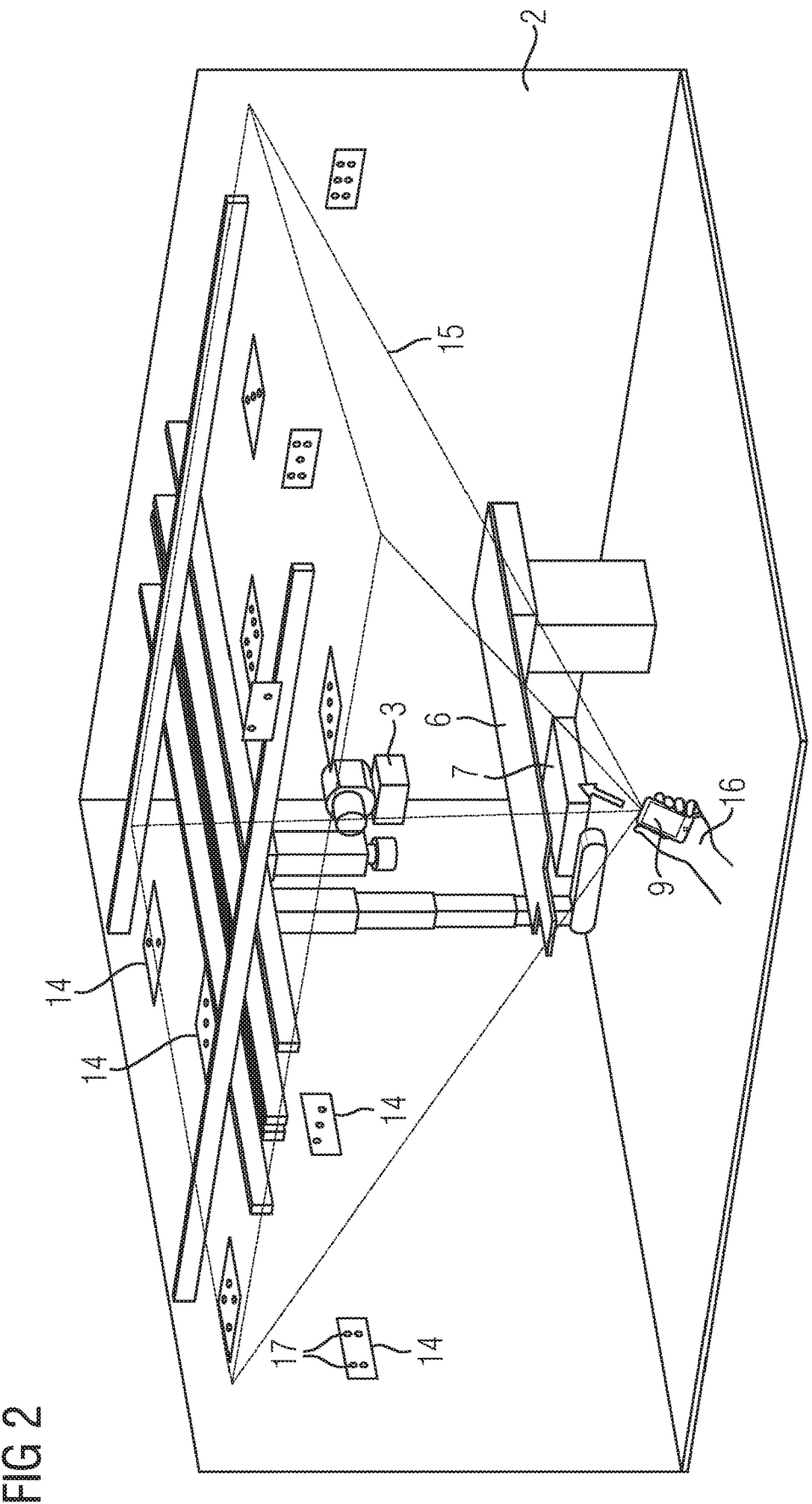
FIG. 2 shows a diagram for determining position data.

FIG. 2 shows a perspective view of the room 2. It firstly shows the medical technology device 1 comprising the patient table 6, the integral unit 3 and the X-ray detector; the collimator 5 is not shown for the sake of clarity. An operator's hand 16 holds the operator device 9 in the room 2, wherein the coverage 15 of the front camera 19 as operator device sensor 12 is indicated. The markers 14 clearly distinguishable in their visually perceptible pattern can be seen at different locations in the room 2, here for the sake of clarity distributed at least over the ceiling and walls; it is obviously also possible for optical markers 14 to be disposed on the floor. The active markers 14 here have infrared LEDs 17 in different patterns.

During operation, operator device position data is continuously generated via the control device 8 to control the collimator 5. Since the position and characteristics of the markers 14 have been determined in a configuration phase and e.g. stored in a database, the markers 14 detected by the camera can be used for position determination, wherein the active markers 14 can be activated via corresponding short-range radio links to output corresponding, detectable signals in synchronization with the operator device 9. The infrared LEDs 17 enable the markers 14 to be reliably detected. To support the sensor data of the camera, the sensor data of accelerometers (tilting in the room), angular rate sensors (motion) and magnetometers (orientation to the north coarsely determinable) as operator device sensors 12 is also taken into account.

The position data of the operator device 9 which is determined in this way can already be understood as operator position information, as the operator is holding the operator device 9 in his/her hand 16. However, it can also be used as the basis for deriving or estimating operator position information, particularly the operator's eyes. For example, a particular offset, a particular operator eye level and a particular viewing direction of the operator can be assumed.

However, in the example embodiment described here, the position data is used directly as position information of the operator in order to serve as a perspective for a three-dimensionally visualizing display on the touchscreen 11 of the operator device 9, which display is used for adjusting the collimator settings.

Figure 3:
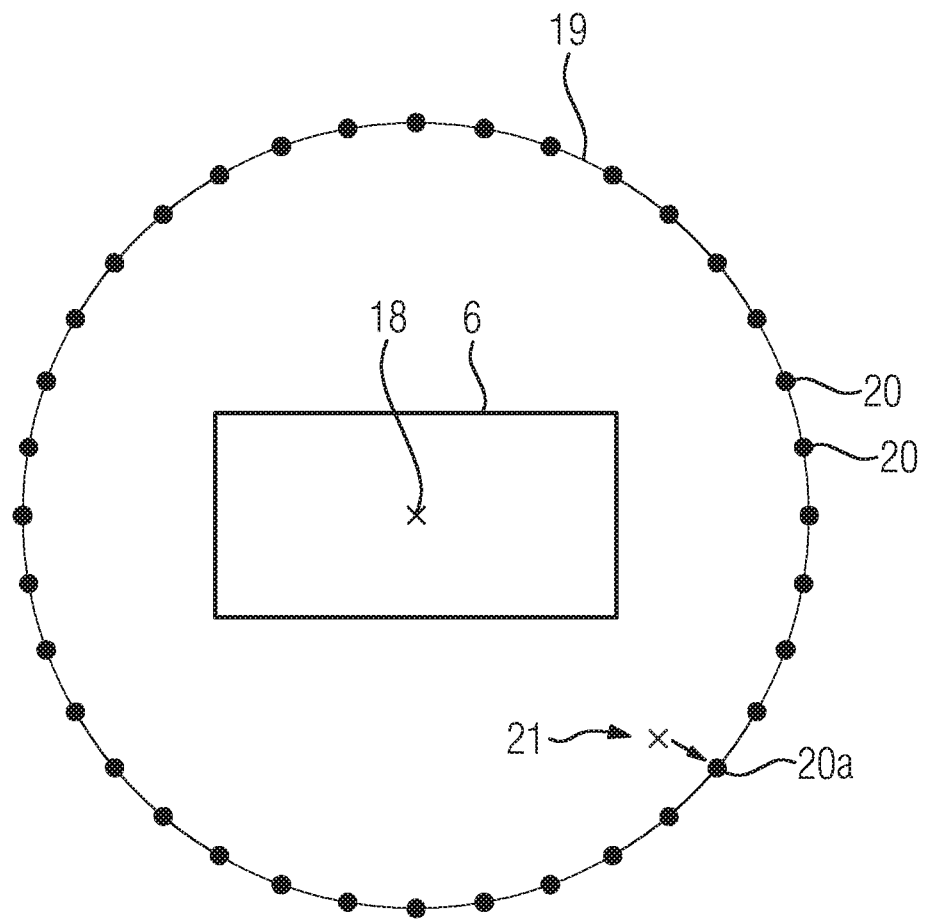
FIG. 3 shows a possible definition of a ring of possible observation points.

As it is known that the operator, when operating the collimator 5, is usually looking in the direction of the patient table 6, specifically at the region of interest, and there are viewing angles with respect to that region that are particularly suitable for adjustments, in order to visualize the beam, in this case, cf. FIG. 3, a reference point 18 of the X-ray device 1 is defined, here the center of the patient table 6 or the point on the patient table 6 where the central ray of the X-ray generator 4 would be incident. A ring 19 of possible observation points 20 extends around the reference point 18, wherein each of the observation points 20 together with a viewing direction with respect to the reference point 18 defines a perspective. The ring 19 is depicted as circular here by way of example which is quite possible as a selection; however, it is also conceivable in principle to use other shapes for the ring, e.g. an elliptical shape, in order to better match the elongated shape of the patient table 6.

The height of the ring 19, i.e. of the observation points 20, above floor level and the at least one radius of the ring 19, i.e. the distance from the observation points 20 to the reference point 18, can be fixed, but can also be dynamically selected, in respect of the distance e.g. as a function of a distance from the reference point 18 described by the position information or rather in the case of a circular shape as the latter or, in the case of the height, as a function of height information of the current operator, which information can be obtained, for example, from an operator input and/or from sensor data showing the operator.

In this example embodiment, fixed perspectives providing an optimum direction-dependent view of the X-ray beam (and in particular the patient table) shall be assumed. Then, to select a perspective for the display to be generated, that of the current operator position 21 described by the position information at the nearest observation point 20*a* is selected, which observation point, as mentioned, together with the viewing direction with respect to reference point 18, defines the perspective.

Figure 4:
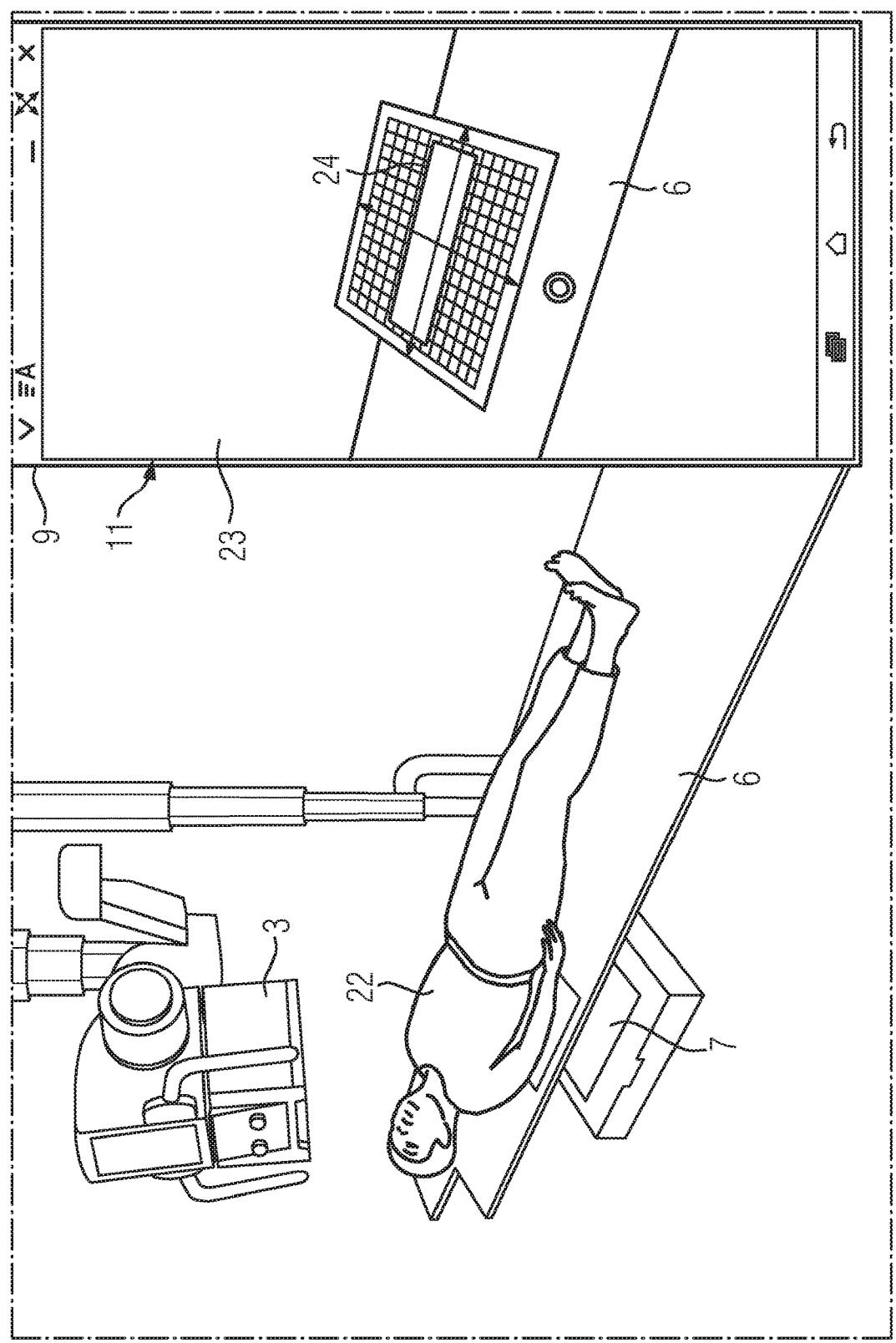
FIG. 4 shows the operator's perspective view of the X-ray device and a correspondingly generated display on the operator device.

FIG. 4 lastly shows side by side the operator's view of the real medical technology device 1 comprising the patient table 6, the integral unit 3 and the X-ray detector 7, wherein a patient 22 to be examined has already been positioned on the patient table 6. Visible on the touchscreen display 11 of the operator device 9 is a display 23 derived from the position information and showing, from the perspective selected according to FIG. 3 (which corresponds at least essentially to the operator's perspective of the real patient table 6) a virtual representation of the patient table 6 and, in the form of a rectangle 24, the resulting X-ray beam for the current collimator settings. By manipulating the rectangle 24 as a display element, the collimator settings can be changed, e.g. the beam can be narrowed or enlarged by gripping the corners, and/or displacement of the integral unit 3 and therefore of the collimator 5 can be achieved by dragging the entire rectangle 24. From the corresponding operator control information on the touchscreen 11, the control device 8 derives control information which causes the collimator 5 to be adjusted accordingly.

As FIG. 4 shows, a particularly intuitive and useful operator aid for controlling the collimator 5 is implemented by way of the coinciding perspectives.

It should also be noted that, to generate another display additionally assisting the operator on the integral unit 3, an overhead view camera 25 (cf. FIG. 1) oriented in the direction of the central ray can be provided so that the display is produced from the angle of view of the X-ray generator 4. The additional display can be selectable by the operator.

Although the invention has been illustrated and described in detail by the preferred example embodiment, the invention is not limited to the examples disclosed and other variations will be apparent to persons skilled in the art without departing from the scope of protection sought for the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

1 X-ray device
2 room
3 integral unit
4 X-ray generator
5 collimator
6 patient table
7 X-ray detector
8 control device
9 operator device
10 smart device
11 touchscreen
12 operator device sensor
13 communication link
14 markers
15 coverage area
16 hand
17 infrared LED
18 reference point
19 ring
20 observation point
20a observation point
21 position
22 patient
23 display
24 rectangle
25 overhead view camera

What is claimed is:

1. A method for a medical imaging X-ray device including an X-ray generator, to which a collimator is assigned, an X-ray detector, a patient table for positioning a patient to be X-rayed, and a wireless, hand-held device of an operator including a touchscreen, the method comprising:
generating a display, visualizing a current setting of the collimator, on the touchscreen;
adjusting settings of the collimator according to operating data describing a manipulation of display elements of the display;
determining position information, describing at least one of a position and orientation of the operator, from sensor data of at least one sensor;
selecting a perspective, using the position information determined, corresponding at least approximately to a viewing angle of the operator with respect to the patient table; and
generating the display for three-dimensionally visualizing, showing an X-ray beam with the settings of collimator adjusted, at the perspective selected.

2. The method as claimed in claim 1, wherein the at least one sensor includes at least one sensor of a camera tracking the operator.

3. The method of claim 1, wherein the determining of the position information, describing at least one of a position and orientation of the wireless, hand-held device of the operator, includes determining position data from the sensor data and deriving the position information from the position data using at least one assumption in respect of the operator.

4. The method as claimed in claim 3, wherein the position data is determined from sensor data, of at least one operator device sensor incorporated in the wireless, hand-held device of the operator.

5. The method of claim 4, wherein the at least one operator device sensor is at least one sensor of a camera, and wherein optical markers, disposed in the room in which the medical imaging X-ray device is disposed, are detected and used in the determining of the position data.

6. The method of claim 5, wherein in addition to the camera, the at least one operator device sensor includes at least one of
at least one accelerometer,
at least one angular rate sensor, and
at least one magnetometer.

7. The method of claim 3, wherein the generating of the display includes using a viewing direction aligned to a reference point of the medical imaging X-ray device.

8. The method of claim 7, wherein at least one of a central point of the patient table and a point of intersection of a central beam with the patient table is selected as the reference point.

9. The method of claim 3, wherein at least one of
upon the operator manipulating corner points of the X-ray beam shown in the display, the settings of the collimator are adjusted to a corresponding beam geometry and,
upon the operator dragging the X-ray beam in the display, the components of the collimator are displaced.

10. The method of claim 1, wherein the generating of the display includes using a viewing direction aligned to a reference point of the medical imaging X-ray device.

11. The method of claim 10, wherein at least one of a central point of the patient table and a point of intersection of a central beam with the patient table is selected as the reference point.

12. The method of claim 11, wherein a ring of observation points around the reference point, defining perspectives selectable in conjunction with the viewing direction to the reference point, is defined, and wherein the perspective described by an observation point, of the ring of observation points, relatively nearest to the position described in the position information, is selected.

13. The method of claim 10, wherein a ring of observation points around the reference point, defining perspectives selectable in conjunction with the viewing direction to the reference point, is defined, and wherein the perspective described by an observation point, of the ring of observation points, relatively nearest to a position described in the position information, is selected.

14. The method of claim 13, wherein a height of the ring, above floor level, is selected according to operator height information, the operator height information being at least one of defined, derivable from the sensor data and specifiable by the operator.

15. The method of claim 1, wherein at least one of
upon the operator manipulating corner points of the X-ray beam shown in the display, the settings of the collimator are adjusted to a corresponding beam geometry and,
upon the operator dragging the X-ray beam in the display, components of the collimator are displaced.

16. The method of claim 1, wherein, to generate an additional display containing a beam, image data of an overhead view camera disposed on at least one of the X-ray generator and the collimator and oriented in a direction of a central ray of the X-ray generator is acquired and the additional display is generated from a point of view of the X-ray generator onto a region of interest.

17. The method of claim 1, wherein the determining of the position information, describing at least one of a position and orientation of the wireless, hand-held device of the operator, includes determining position data from the sensor data and deriving the position information from the position data using at least one of a height and viewing direction of the operator.

18. An X-ray device, comprising:
an X-ray generator, a collimator being assigned to the X-ray generator;
an X-ray detector;
a patient table to position a patient to be X-rayed;
a wireless, hand-held operator device including a touchscreen; and
a controller, designed to:
generate a display, visualizing a current setting of the collimator, on the touchscreen,
adjust settings of the collimator according to operating data describing a manipulation of display elements of the display,
determine position information, describing at least one of a position and orientation of the operator, from sensor data of at least one sensor,
select a perspective, using the position information determined, corresponding at least approximately to a viewing angle of an operator with respect to the patient table, and
generate the display for three-dimensionally visualizing on the touchscreen, showing an X-ray beam with the settings of the collimator adjusted, at the perspective selected.

* * * * *